United States Patent
Herron et al.

(10) Patent No.: US 7,011,871 B2
(45) Date of Patent: Mar. 14, 2006

(54) CHARGE TRANSPORT COMPOUNDS AND ELECTRONIC DEVICES MADE WITH SUCH COMPOUNDS

(75) Inventors: Norman Herron, Newark, DE (US); Brian D. Hoyt, Newark, DE (US); Nora Sabina Radu, Landenberg, PA (US); Eric Maurice Smith, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/783,132

(22) Filed: Feb. 20, 2004

(65) Prior Publication Data

US 2005/0186495 A1   Aug. 25, 2005

(51) Int. Cl.
*C09K 11/06* (2006.01)
*C09K 19/54* (2006.01)
*H01J 1/63* (2006.01)
*C07D 209/82* (2006.01)

(52) U.S. Cl. .................. 428/1.4; 428/690; 428/917; 252/299.5; 313/504; 313/506; 548/440; 548/444

(58) Field of Classification Search ............... 428/1.4, 428/690, 917; 313/504, 506; 252/299.5; 548/440, 444
See application file for complete search history.

(56) References Cited

U.S. PATENT DOCUMENTS

| | | |
|---|---|---|
| 4,952,667 A | 8/1990 | Shikatani et al. |
| 5,116,995 A | 5/1992 | Nakazato et al. |
| 5,652,067 A | 7/1997 | Ito et al. |
| 5,736,284 A | 4/1998 | Kobayashi et al. |
| 5,792,557 A | 8/1998 | Nakaya et al. |
| 5,891,587 A | 4/1999 | Hu et al. |
| 6,005,085 A | 12/1999 | Ueno et al. |
| 6,066,426 A | 5/2000 | Mott et al. |
| 6,140,004 A | 10/2000 | Mott et al. |
| 6,451,461 B1 | 9/2002 | Lee et al. |
| 6,514,968 B1 | 2/2003 | TenBrink |
| 6,528,657 B1 | 3/2003 | Nakaya et al. |
| 6,635,364 B1 | 10/2003 | Igarashi |
| 6,657,084 B1 | 12/2003 | Hosokawa et al. |
| 6,670,054 B1 | 12/2003 | Hu et al. |
| 6,686,067 B1 | 2/2004 | Li et al. |
| 2002/0107405 A1 | 8/2002 | Lin et al. |
| 2002/0172885 A1 | 11/2002 | Nagai et al. |
| 2003/0023099 A1 | 1/2003 | Nakaya et al. |
| 2003/0092880 A1 | 5/2003 | Leclerc et al. |
| 2003/0205696 A1 | 11/2003 | Thorns et al. |
| 2003/0207188 A1 | 11/2003 | Jubran et al. |
| 2003/0214228 A1 | 11/2003 | Itou |
| 2004/0115476 A1 * | 6/2004 | Oshiyama et al. .......... 428/690 |

FOREIGN PATENT DOCUMENTS

| | | |
|---|---|---|
| JP | 2003031371 A | 1/2003 |
| WO | WO 03/078541 A1 | 9/2003 |
| WO | WO 03/080760 A1 | 10/2003 |
| WO | WO 03/080761 A1 | 10/2003 |

* cited by examiner

*Primary Examiner*—Shean C. Wu

(57) ABSTRACT

The present invention relates to novel compounds useful as electronic hole transport materials, and to compositions and electronic devices comprising at least one layer containing the compositions.

13 Claims, 1 Drawing Sheet

CHARGE TRANSPORT COMPOUNDS AND ELECTRONIC DEVICES MADE WITH SUCH COMPOUNDS

BACKGROUND OF THE INVENTION

1. Field of the Invention

The present invention relates to novel compounds useful as host materials in making electronic devices. The invention further relates to electronic devices having at least one active layer comprising such a host material.

2. Background

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

Certain properties of materials used in films in electronic devices rely on a relatively high Tg in addition to the ability to form films.

CBP and mCP are commonly used as host materials in OLEDs; however they have limitations. CBP has a modest Tg and has a low lying triplet energy, making it a poor host for deep blue phosphorescent emissive systems. mCP has a higher triplet energy, making it more suitable for blue emissive systems, but has an undesirably low Tg.

There is a continuing need for host materials for use in electronic devices.

SUMMARY OF THE INVENTION

The compounds disclosed herein are useful in making charge transport layers for use in electronic devices. The charge transport layers can be used in any application wherein charge transport capacity is desired.

One aspect of the present invention is a compound having the formula:

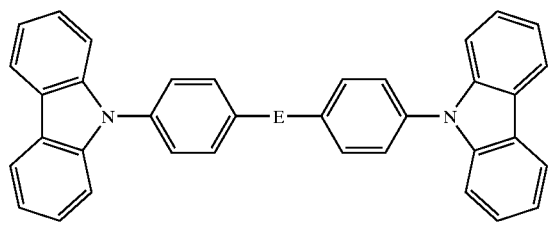

(I)

wherein E is selected from O, S, $(SiR^1R^2)_m$ wherein m is an integer of 1 to 20, $(CR^1R^2)_m$ wherein m is an integer of 1 to 20, and combinations thereof, and can be different at each occurrence, wherein $R^1$ and $R^2$ are each independently selected from H, F, alkyl, aryl, alkoxy, aryloxy, fluoroalkyl, fluoroaryl, fluoroalkoxy, and fluoroaryloxy, and wherein $R^1$ and $R^2$ can, when taken together, form a non-aromatic ring.

Another aspect of the present invention is a composition comprising a compound having the formula:

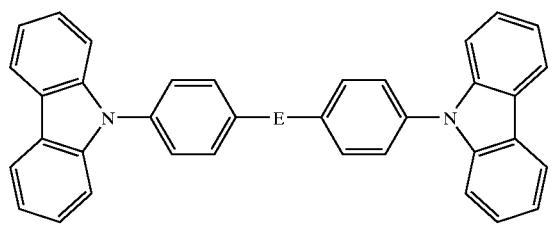

(I)

wherein E is selected from O, S, $(SiR^1R^2)_m$ wherein m is an integer of 1 to 20, $(CR^1R^2)_m$ wherein m is an integer of 1 to 20, and combinations thereof, and can be different at each occurrence, wherein $R^1$ and $R^2$ are each independently selected from H, F, alkyl, aryl, alkoxy, aryloxy, fluoroalkyl, fluoroaryl, fluoroalkoxy, and fluoroaryloxy, and wherein $R^1$ and $R^2$ can, when taken together, form a non-aromatic ring.

A further aspect of the invention is an electronic device comprising a composition comprising a compound having the formula (I):

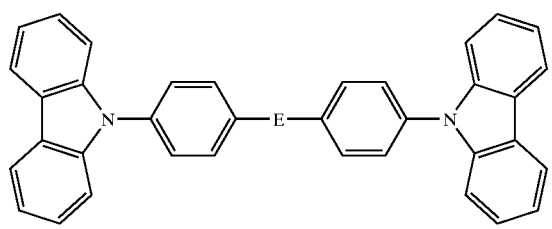

(I)

wherein E is selected from O, S, (SiR¹R²)$_m$ wherein m is an integer of 1 to 20, (CR¹R²)$_m$ wherein m is an integer of 1 to 20, and combinations thereof, and can be different at each occurrence, wherein R¹ and R² are each independently selected from H, F, alkyl, aryl, alkoxy, aryloxy, fluoroalkyl, fluoroaryl, fluoroalkoxy, and fluoroaryloxy, and wherein R¹ and R² can, when taken together, form a non-aromatic ring.

In some embodiments, an electronic device made using the compounds disclosed herein is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and diode.

The foregoing general description and the following detailed description are exemplary and explanatory only and are not restrictive of the invention, as defined in the appended claims.

DESCRIPTION OF THE DRAWINGS

The invention is illustrated by way of example and not limitation in the accompanying figures.

DETAILED DESCRIPTION OF THE PREFERRED EMBODIMENTS

Figure 1:
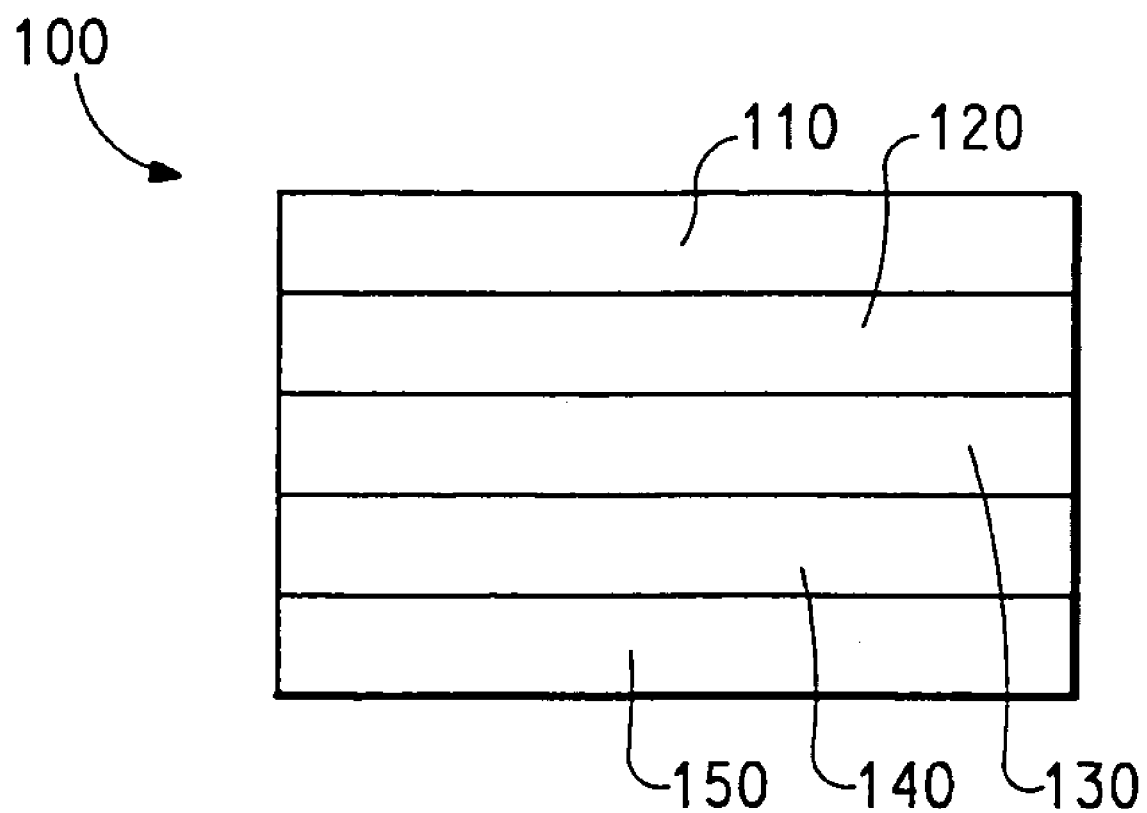
FIG. 1: An illustrative example of one organic electronic device comprising at least one layer comprising a novel compound as disclosed herein.

Compositions containing the compounds disclosed herein are useful in electronic devices such as, for example, OLEDs, particularly as host materials therefor.

The compounds disclosed herein are carbazole derivatives. One class of compounds is compounds having formula (I):

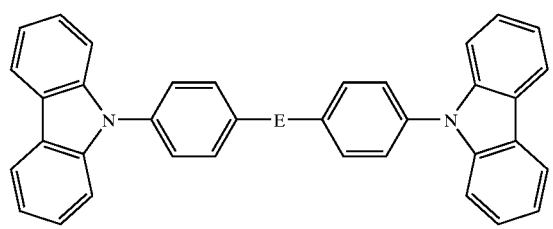

(I)

wherein E is selected from O, S, (SiR¹R²)$_m$ wherein m is an integer of 1 to 20, (CR¹R²)$_m$ wherein m is an integer of 1 to 20, and combinations thereof, and can be different at each occurrence, wherein R¹ and R² are each independently selected from H, F, alkyl, aryl, alkoxy, aryloxy, fluoroalkyl, fluoroaryl, fluoroalkoxy, and fluoroaryloxy, and wherein R¹ and R² can, when taken together, form a non-aromatic ring.

An exemplary compound is represented by formula (II):

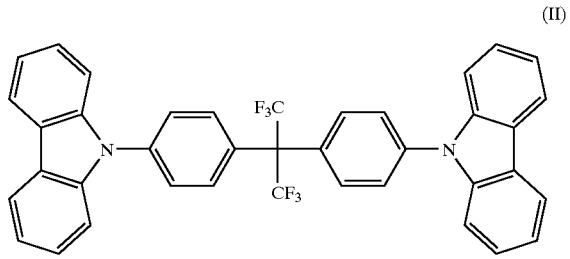

(II)

which exemplifies a compound of formula (I), wherein E is (CR¹R²)$_m$, m is 1, and R¹ and R² are trifluoromethyl. A further exemplary compound has the formula (III):

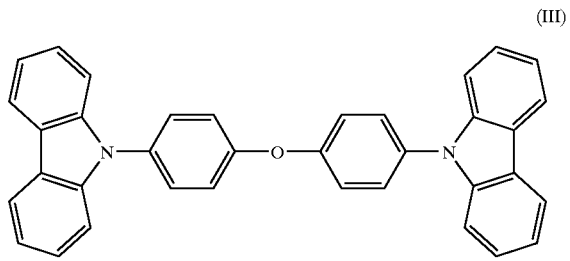

(III)

which exemplifies a compound of formula (I) wherein E is O.

Also within the scope of the present invention are compounds having the formula (IV):

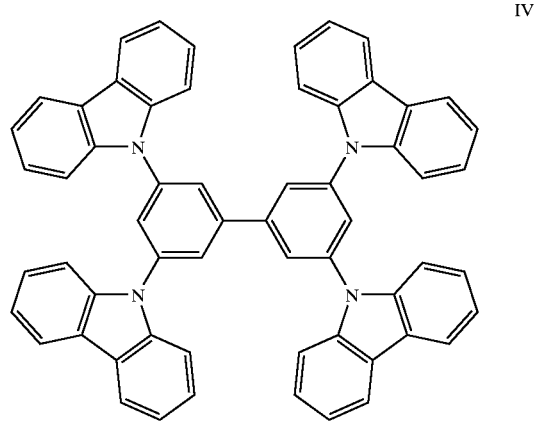

IV

For making electronic devices, including OLED devices, it is desirable that the compounds form films when deposited onto a transparent anode such as indium-doped tin oxide (ITO). The quality of the resultant film can be superficially judged by visual/microscopic inspection for smoothness and defect density. It is desirable that visually observed defects be minimal. Furthermore, film quality can be measured by estimation of film thickness over several separate areas of the film using, for example, an optical ellipsometer or a mechanical profilometer; it is desirable that the films have substantially uniform thicknesses as measured in the different areas of the film.

The compounds can be used in liquid form, such as a dispersion or solution, in making electronic devices. An exemplary process for making an electronic device includes: providing a liquid comprising a compound having the formula (I) as described hereinabove; providing an anode; contacting said liquid comprising said compound with said anode; Removing said liquid from said compound to produce a hole transport film; providing an emitter; disposing said emitter adjacent to said hole transport film; providing an electron transporter and disposing said electron transporter adjacent to said emitter; and providing a cathode adjacent to said electron transporter.

The liquid is, in some embodiments, a solvent for the compound. A suitable solvent for a particular compound or related class of compounds can be readily determined by one skilled in the art. For some applications, it is desirable that the compounds be dissolved in non-aqueous solvents. Such non-aqueous solvents can be relatively polar, such as C1 to C20 alcohols, ethers, and acid esters, or can be relatively non-polar such as C1 to C12 alkanes or aromatics such as toluene, xylenes, trifluorotoluene and the like. Other suitable liquids for use in making the liquid composition, either as a solution or dispersion as described herein, comprising the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methylpyrrolidone) esters (such as ethylacetate) alcohols (isopropanol), keytones (cyclopentatone) and mixtures thereof.

In one embodiment, the compound is dissolved in a solvent in which the compound is substantially soluble, e.g., sufficiently soluble to form a solution. The solution is then formed into a thin film and dried by any of several techniques such as spin-coating, inkjetting etc. The resultant film formed as the solvent evaporates is then further dried by baking at elevated temperatures above the boiling point of the solvent either in a vacuum of nitrogen atmosphere. The film is then subjected to further processing by depositing a second solution containing emissive layer materials on top of the pre-formed compound film where the emissive materials are dissolved in a solvent in which the compound is substantially insoluble. By "substantially insoluble" is meant that less than about 5 mg of the compound dissolves in 1 ml of the solvent. However, solubilities greater than or less than 5 mg can be used and may be desirable for some applications. For example, a modest solubility up to 10 mg/mL may result in a blurred or graded interface between the HTM polymer of the present invention and the emissive layer materials. Such blurring can have deleterious or beneficial effects depending upon the natures of the materials involved. Such blurring of the interface can result in improved charge transport across the interface and substantially improved device performance or lifetime.

As will be recognized by one skilled in the art, the solubility of a compound is determined in part by substituent groups within the compound. In particular, in the compounds disclosed herein, the nature of the group "E" in the compound can be varied in order to control the solubility of a compound in a particular solvent or class of solvents. Thus, by varying the nature of the group "E", a compound can be modified such that is more or less soluble in water or any given organic non-aqueous solvent.

For making electronic devices, it is desirable that the compounds have a relatively low solubility, e.g., a solubility less than about 5 mg/mL, even about 2 mg/mL or less, in solvents that can be used to deposit an emissive layer layer film onto an electrode, which is typically a transparent anode such as ITO (indium doped tin oxide).

The present invention also relates to electronic devices comprising at least one layer containing a composition as disclosed herein, as a hole transport layer. The compositions can be in a separate layer, positioned between a photoactive layer and an electrode. Alternatively, a photoactive layer of an organic electronic device can contain the composition. An example of an electronic device that can contain a composition as disclosed herein is shown in FIG. 1. The device 100 has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. In the illustrated embodiment, the device has an optional additional transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary,* 470 and 476 (McGraw-Hill, Inc. 1966).

The compounds disclosed herein are particularly useful in the hole transport layer 120, and as a charge conducting host in the photoactive layer, 130. The other layers in the device can be made of any materials that are known to be useful in such layers. The anode, 110, is an electrode that is particularly efficient for injecting positive charge carriers. It can be made of, for example, materials containing a metal, mixed metal, alloy, metal oxide or mixed-metal oxide, a conducting polymer, or a combination or mixture thereof. Suitable metals include the Group 11 metals, the metals in Groups 4, 5, and 6, and the Group 8–10 transition metals. If the anode is to be light-transmitting, mixed-metal oxides of Group 12, 13 and 14 metals, such as indium-tin-oxide, are generally used. The anode 110 can also comprise an organic material such as polyaniline, as described, for example, in "Flexible light-emitting diodes made from soluble conducting polymer," *Nature* vol. 357, pp 477–479 (11 Jun. 1992). At least one of the anode and cathode is typically at least partially transparent to allow the generated light to be observed.

Examples of the photoactive layer 130 include all known electroluminescent materials, including fluorescing and phosphorescing materials (including both organo-metallic complexes and conjugated polymers). Organometallic electroluminescent compounds are desirable for some applications. Specific useful compounds include cyclometalated iridium and platinum electroluminescent compounds and mixtures thereof. Complexes of Iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications U.S. 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1–3), 379–383, and Campbell et al., in Phys. Rev. B, Vol. 65 085210. Examples of a few suitable iridium complexes are given in FIG. 6, as Formulae IV(a) through IV(e). Analogous tetradentate platinum complexes can also be used. These electroluminescent complexes can be used alone, or doped into charge-carrying hosts, as noted above. The compounds, in addition to being useful in the hole transport layer 120, electronic transport layer 140/150 can also act as a charge carrying host for an emissive dopant in the photoactive layer 130 or otherwise part of the photoactive layer.

Examples of electron transport materials which can be used in layer 140 and/or layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers can generally be accomplished by balancing the goals of providing a device with high device efficiency with device operational lifetime.

It is understood that each functional layer may be made up of more than one layer.

The devices can be prepared using a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied from solutions or dispersions in suitable solvents, using any conventional coating or printing technique, including but not limited to spin-coating, dip-coating, roll-to-roll techniques, ink-jet printing, screen-printing, gravure printing and the like. Combinations of vapor deposition and solution coating of individual layers can be used. In general, the different layers will have the following range of thicknesses: anode 110, 500–5000 Å, frequently 1000–2000 Å; hole transport layer 120, 50–2000 Å, frequently 200–1000 Å; photoactive layer 130, 10–2000 Å, frequently 100–1000 Å; electron transport layer 140 and 150, 50–2000 Å, frequently 100–1000 Å; cathode 160, 200–10000 Å, frequently 300–5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

Examples of some uses include, but are not limited to, organic light-emitting diodes ("OLED"s), photovoltaic cells, light sensors, thin film organic transistors, photoconductors, and electrophotographic applications. Examples of organic electronic devices that may benefit form having one or more layers comprising the new compounds and compositions described herein include: (1) devices that convert electrical energy into radiation (e.g., a light-emitting diode, light emitting diode display, or diode laser), (2) devices that detect signals through electronics processes (e.g., photodetectors (e.g., photoconductive cells, photoresistors, photoswitches, phototransistors, phototubes), IR detectors, (3) devices that convert radiation into electrical energy, (e.g., a photovoltaic device or solar cell), and (4) devices that include one or more electronic components that include one or more organic semi-conductor layers (e.g., a transistor or diode).

Unless otherwise expressly stated, the following terms when used herein shall be interpreted to have the definitions set forth below.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "the", "a" or "an" are employed to describe elements and components of the invention. This is done merely for convenience and to give a general sense of the invention. This description should be read to include one or at least one and the singular also includes the plural unless it is obvious that it is meant otherwise.

As used herein, the term "charge transport composition" is intended to mean material that can receive a charge from an electrode and facilitate its movement through the thickness of the material with relatively high efficiency and small loss of charge. Hole transport compositions are capable of receiving a positive charge from an anode and transporting it. Electron transport compositions are capable of receiving a negative charge from a cathode and transporting it.

The term "composition", used alone to refer to compositions having particular formulas disclosed and claimed herein, is intended to be construed broadly to include the compounds, monomers, dimers, oligomers and polymers thereof, as well as solutions, dispersions, liquid and solid mixtures and admixtures.

The term "anti-quenching material" is intended to mean a material which prevents, retards, or diminishes both the transfer of energy and the transfer of an electron to or from the excited state of the photoactive layer to an adjacent layer.

The term "photoactive" refers to any material that exhibits electroluminescence, photoluminescence, and/or photosensitivity.

The term "group" is intended to mean a part of a compound, such as a substituent in an organic compound. The prefix "hetero" indicates that one or more carbon atoms have been replaced with a different atom.

The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted.

The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted.

Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "compound" is intended to mean an electrically uncharged substance made up of molecules that further consist of atoms, wherein the atoms cannot be separated by physical means.

The term "polymeric" is intended to encompass oligomeric species and include materials having 2 or more monomeric units. In addition, the IUPAC numbering system is used throughout, where the groups from the Periodic Table are numbered from left to right as 1 through 18 (CRC Handbook of Chemistry and Physics, 81$^{st}$ Edition, 2000).

As used herein, "solution processing" means processes that include depositing from a liquid medium. The liquid medium can be in the form of a solution, a dispersion, an emulsion, or other forms.

The term "film" refers to a coating covering a desired area. The area can be as large as an entire display, or as small as a single sub-pixel. Films can be formed by any conventional deposition technique. Typical deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following examples illustrate certain features and advantages of the present invention. They are intended to be illustrative of the invention, but not limiting. All percentages are by weight, unless otherwise indicated.

Example 1

Preparation of 3,3',5,5'-tetracarbazole-biphenyl.

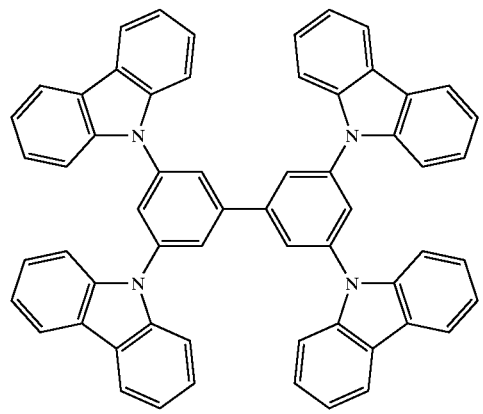

4.61 g of 3,3',5,5'-tetrabromobiphenyl, 7.22 g carbazole, 2.75 g copper powder, 2.28 g 18-crown-6 and 11.94 g potassium carbonate were combined under nitrogen in a dry box in a 1-neck round-bottomed flask equipped with a stir bar, condenser, and septum. The flask was sealed and placed under positive $N_2$ pressure and heated to reflux. After 42 hours the reaction appeared to be complete by thin layer chromatography (TLC) on silica using methylene chloride as eluent. Unreacted carbazole was still present, but the tetrabromobiphenyl was completely consumed.

The crude material obtained was washed with water, extracted with ether, and concentrated to a brown solid. This solid was dissolved in dichloromethane/hexanes 1:1 and filtered through a column of silica gel leaving a dark band at the top. 4 spots were present as detected by TLC on silica gel after the filtration. The material was dissolved in hot toluene and rapidly precipitated with the addition of methanol. This was repeated with THF and methanol 4 more times. At this point an NMR spectrum is taken. The material is white. Yield 7.0 g 88%.

Example 2

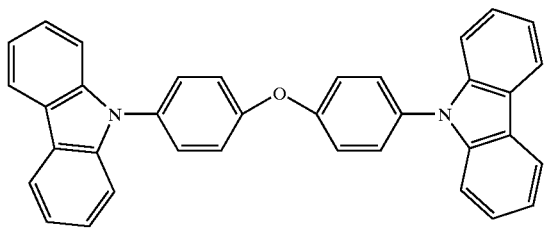

All manipulations were performed under an inert atmosphere of nitrogen. A Schlenk flask equipped with a condenser was charged with 4-bromophenylether (3.90 g), carbazole (4.34 g), 18-crown-6 (0.70 g), Cu (1.65 g) and $K_2CO_3$ (3.60 g) and 1,2-dichlorobenzene (150 mL). The resulting mixture was heated to 180 C for four days. After cooling to room temperature, water was added and the mixture was stirred overnight. The organic layer was isolated and the water layer was washed with water. The combined organic layers were dried over $MgSO_4$ and the solvent was evaporated to give a brown oil. The desired product was isolated by crystallization from $CH_2Cl_2$/MeOH to give an off-white powder in 58% yield (3.5 g). $^1H$ NMR ($CD_2Cl_2$, 500 MHz): δ 8.14 (d, 1H), 7.58(d, 1H), 7.42 (m, 2H), 7.35 (d, 1H), 7.27 (m, 1H).

Example 3

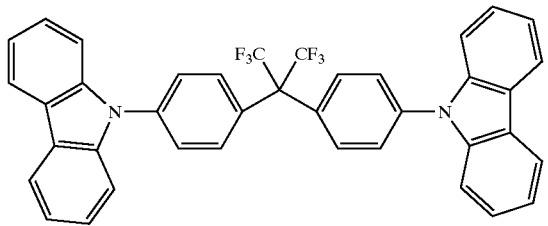

All manipulations were performed under an inert atmosphere of nitrogen. A Schlenk flask was charged with 4,4'-[bis(p-trifluoromethane sulphoxy)phenyl](hexafluoropropylidine) (5.20 g), carbazole (2.90 g), tris(dibenzylideneacetone) dipalladium (0.424 g), 2-dicyclohexylphosphino-2'-(N,N'-dimethylamino)biphenyl (0.36 g), $K_3PO_4$ (4.96 g) and toluene (50 mL). The resulting mixture was heated to 95 C for two days. After cooling to room temperature, the reaction mixture was diluted with toluene and $CH_2Cl_2$ and filtered through a pad of celite/silica. The solvent was removed by rotary evaporation and the product was recrystallized from hot toluene to give a white powder in 25% yield (1.35 g). $^{19}F$ NMR ($CD_2Cl_2$): δ −64.25.

What is claimed is:
1. A compound having the formula

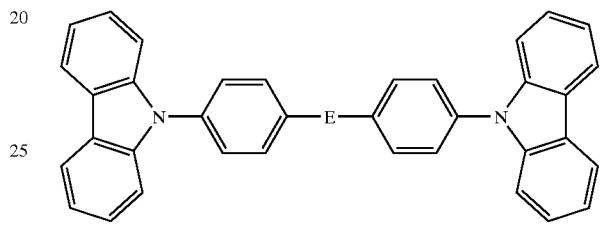

wherein E is selected from O, S, and $(SiR^1R^2)_m$ wherein m is an integer of 1 to 20 wherein $R^1$ and $R^2$ are each independently selected from H, F, alkyl, aryl, alkoxy, aryloxy, fluoroalkyl, fluoroaryl, fluoroalkoxy and fluoroaryloxy.

2. A composition comprising a compound of claim 1.

3. An electronic device comprising at least one layer comprising the compound of claim 1.

4. The electronic device of claim 3, wherein the electronic device is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and diode.

5. A compound having the formula:

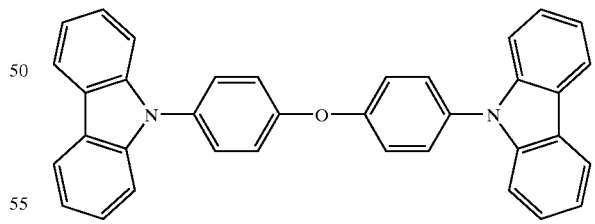

6. A composition comprising a compound of claim 5.

7. An electronic device comprising at least one layer comprising the compound of claim 5.

8. An electronic device of claim 7, wherein the electronic device is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and diode.

9. A compound having the formula:

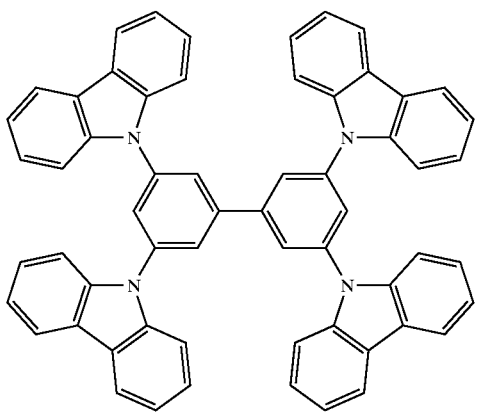

10. A composition comprising the compound of claim 9.

11. An electronic device comprising the compound of claim 9.

12. The electronic device of claim 11, wherein the electronic device is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and diode.

13. A compound having the formula

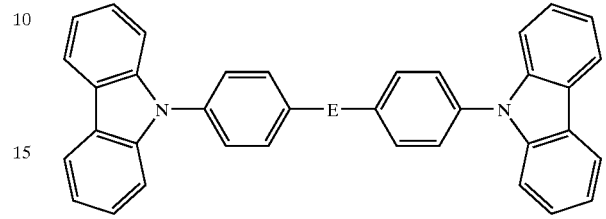

wherein E is selected from $(CR^1R^2)_m$ wherein m is an integer of 1 to 20, wherein $R^1$ and $R^2$ are each independently F, alkoxy, aryloxy, fluoroalkoxy, and fluoroaryloxy.

* * * * *